(12) United States Patent
Morgenstjerne

(10) Patent No.: US 6,368,556 B1
(45) Date of Patent: Apr. 9, 2002

(54) APPARATUS FOR OPERATIONAL CLEANING OF DENTAL HANDPIECES

(75) Inventor: Per Morgenstjerne, Lystrup (DK)

(73) Assignee: Akeda Dental A/S, Risskov (DK)

( * ) Notice: Subject to any disclaimer, the term of this patent is extended or adjusted under 35 U.S.C. 154(b) by 0 days.

(21) Appl. No.: 09/440,264

(22) Filed: Nov. 15, 1999

Related U.S. Application Data

(63) Continuation of application No. 08/765,684, filed on Dec. 30, 1996, now abandoned.

(30) Foreign Application Priority Data

Jun. 28, 1994 (DK) ................................................ 0770/94

(51) Int. Cl.$^7$ ................................................ A61L 2/07
(52) U.S. Cl. .................... 422/26; 422/297; 422/299; 134/102.2; 134/102.3; 134/170
(58) Field of Search ............................. 422/22, 26, 27, 422/28, 29, 33, 292, 295, 297–300, 305, 307; 134/102.1, 102.2, 102.3, 170

(56) References Cited

U.S. PATENT DOCUMENTS

| | | | |
|---|---|---|---|
| 4,552,163 A | 11/1985 | Biancalana et al. | 134/100 |
| 5,057,283 A | 10/1991 | Guggenheim et al. | 422/116 |
| 5,197,499 A | 3/1993 | Bodenmiller et al. | 134/95.2 |
| 5,348,711 A | 9/1994 | Johnson et al. | 422/300 |
| 5,380,369 A | 1/1995 | Steinhauser et al. | 134/1 |
| 5,520,862 A * | 5/1996 | Bowen | 422/295 |
| 5,533,539 A | 7/1996 | Sutter et al. | 134/299 |
| 5,543,119 A | 8/1996 | Sutter et al. | 422/299 |
| 5,552,113 A | 9/1996 | Jennings | |
| 5,571,448 A | 11/1996 | Beerstecher et al. | 422/297 |

FOREIGN PATENT DOCUMENTS

| | | |
|---|---|---|
| EP | 0 403 422 | 12/1990 |
| EP | 0 580 569 | 1/1994 |

OTHER PUBLICATIONS

TECVAC Medical brochure dated Jan. 26, 1999.

* cited by examiner

*Primary Examiner*—Elizabeth McKane
(74) *Attorney, Agent, or Firm*—Nixon Peabody LLP; David S. Safran

(57) ABSTRACT

An apparatus for operative cleaning and preparation of dental handpieces is made as an integrated unit having holding stubs (6) for receiving the handpieces inside a treating chamber (1, 30), which is designed in a pressure resisting manner and with heating means (12, 56) such that it is directly usable for autoclave treatment of the handpieces. Through the holding stubs (6) and in accordance with a control program it is possible to supply warm water and oil to the respective channels in the handpieces. The apparatus may appear as a table unit (32) holding all what is required for a complete cleaning lubrication and sterilization cycle.

14 Claims, 3 Drawing Sheets

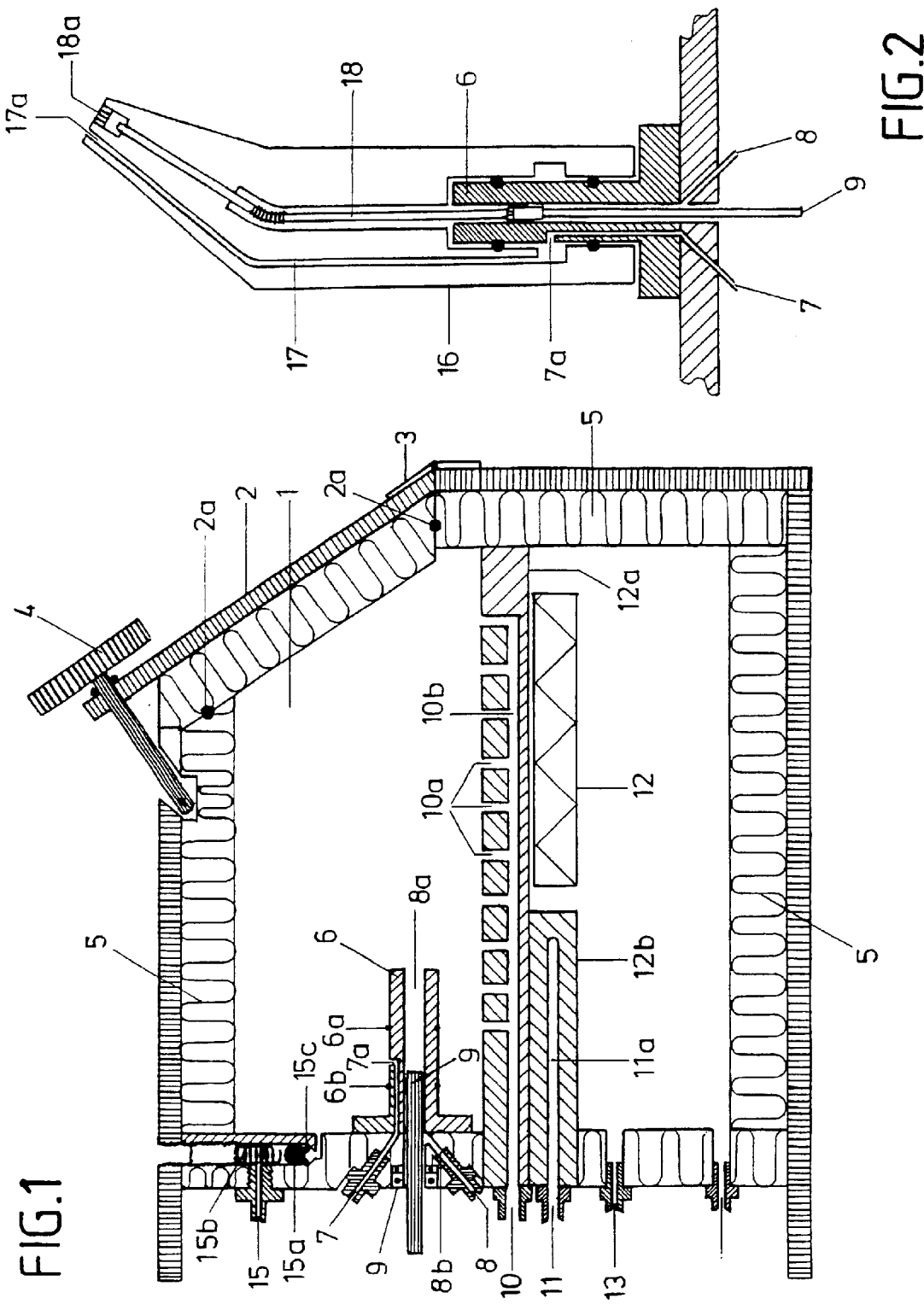

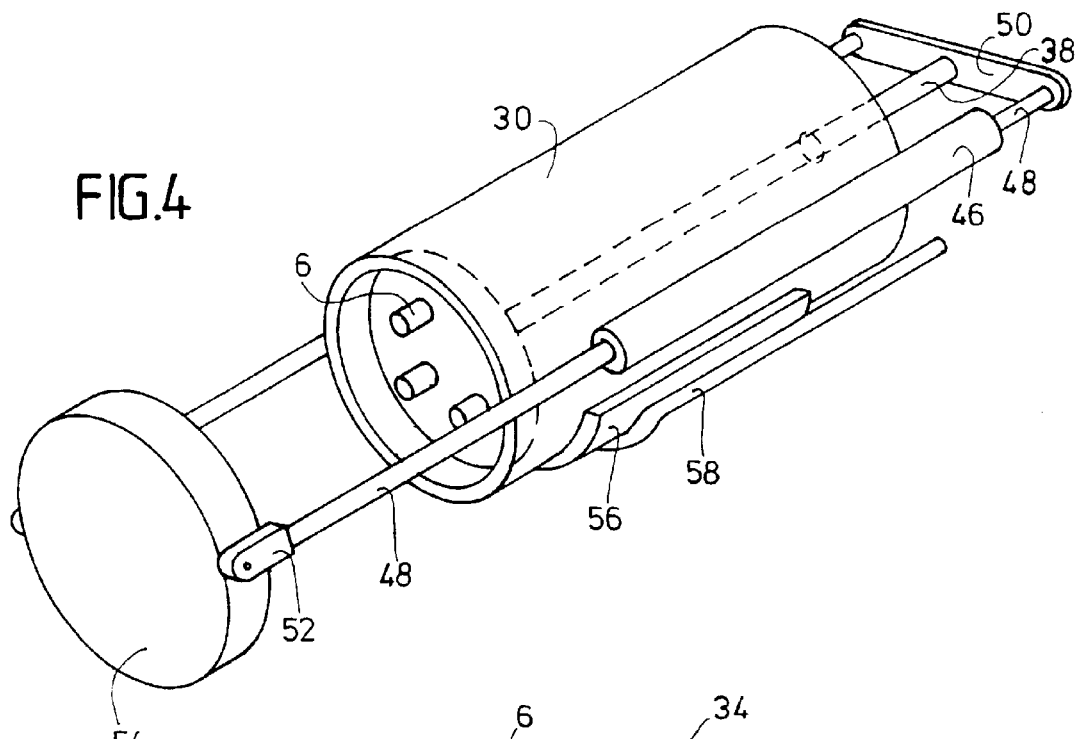
FIG.4
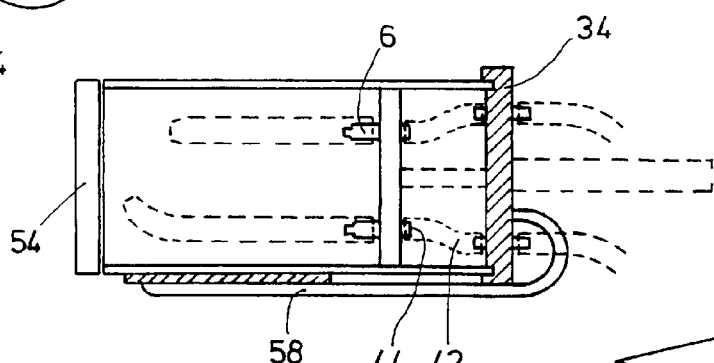
FIG.5
FIG.7
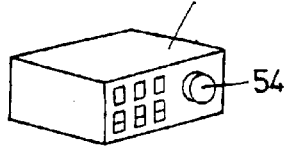
FIG.6
| | PRETREATMENT | AUTOCLAVE TREATMENT | AFTER-TREATMENT |
|---|---|---|---|
| TIME START 0        1 | | 2    4    6    8 | FINISH |
| TEMP. | | | |
| PRESSURE | | | |
| SPRAY | ▨▨▨▨▨▨ | | |
| AIR | ▨▨▨▨ | | ▨▨ |
| ROTATION | ▨▨▨▨ | | ▨▨ |
| LUBRICATION | ▨ | | ▨ |
| DRYING | | | ▨▨ |
| DOOR | ▨ | | ▨ |

APPARATUS FOR OPERATIONAL CLEANING OF DENTAL HANDPIECES

This application is a Continuation of Application Ser. No. 08/765,684, filed Dec. 30, 1996, now abandoned.

The present invention relates to equipment for cleaning, sterilizing and lubricating dental handpieces and contra angles, including turbines.

Handpieces and contra-angles, including, turbines, are relatively complicated instruments which, via a hose system, are supplied with both air and water to the so-called spray channels, and compressed air to turbine instruments, while for certain instruments even a moment of rotation is transferred via a mechanical coupling. During the use of an instrument, e.g. for drilling, a flow of air and water is blown out through the respective spray channels against the drilling spot. The supply of air and water, which may be individually adjusted, has the purpose of cooling and cleaning the drilling spot. When the drilling function is stopped, also the air and water supply are stopped, and a brief suction through the channels prevents afterdripping of water from the water channel. By this suction, liquid from the mouth of the patient may be sucked into the spray channels. It may be both spit and blood, which is blown out again when the instrument is restarted. This is acceptable during the treatment of the individual patient, but of course not by the initial treatment of a new patient, in particular because there may be infectious matter in the sucked-up liquid from the preceding patient, Likewise, disease carriers may remain at the outside of the instrument. Therefore, it is a rising demand that these instruments undergo a cleaning and sterilising process before each initial patient treatment.

By way of example, this process may be carried out by firstly effecting an exterior mechanical cleaning of the instruments, secondly a through-blowing of the interior parts with compressed air and a spray lubrication of the movable parts, whereafter the instruments are placed in an autoclave as already used for the autoclaving of other relevant equipment. Such an autoclaving is very important because even after the flushing of the said channels, these may still hold germ remnants. When the dentist has at disposal more sets of the discussed instruments, there may at any time be instruments ready for use, whilst one or more sets may be under cleaning and autoclaving.

The manual work in connection with the cleaning and lubrication of the instruments can be rather troublesome, and different auxiliaries have already been developed, even including an apparatus which can do the job in a semi or fully automatical manner, requiring the instruments to be mounted on holding stubs provided with supply channels for cleaning and lubricating liquids from respective sources. Thereby the work is facilitated, as it is sufficient to insert the instruments and later on, when they are ready, take them out for final treatment in the autoclave.

However, this treatment of the instruments is not fully suitable, inter alia because the applied cleaning liquids are of such a character that they act decomposingly on the non-metallic parts, e.g. gaskets. Also, the cleaning liquids are not fully effective against all kinds of deposits, and the entire cleaning procedure runs over a rather long period of time. Moreover, the applied cleaning liquids are toxic and only desinfecting—not sterilizing. Thus, exsuction from these apparatuses is required.

The invention has for its purpose to provide for an apparatus enabling a more efficient cleaning, sterilizing and lubrication of the discussed instruments.

The invention is based on the basic consideration that it will be highly advantageous to make use of a heat generator in such a cleaning equipment, because it is then possible to make use of hot water/steam for the flushing of the channels, which has been found to have a high cleaning effect, and also because the entire equipment can then be designed as one single apparatus housing or constituting the required autoclave, which, in a very simple manner, may consist of the chamber in which the instruments are mounted on the said holding stubs. This chamber will be adapted especially for receiving the relevant instruments, so with a pressure tight construction it will constitute an ideal, integrated autoclave combined with an operative treatment chamber receiving the impurities blown out of the instruments. This treatment chamber may be connected with the required drainage means and otherwise be suitable designed for the particular purpose.

With such as apparatus it will be a further possibility to initiate the cleaning by letting oil through the rotating parts of the instruments, this being effectively loosening for many impurities, not least for solidified oil remnants. It is possible to operate with compressed air, oil, water and air and, optionally, hot steam, whereby there are different possibilities making the use of special cleaning liquids superfluous, and even removing the need of exsuction. The cleaning can be effected rapidly and effectively, and not least the integrated autoclavation in a small and quickly heated chamber will imply a noticeably reduced process time with a low energy consumption.

Since the described process proceeds automatically, time is made free for the assistant, who will usually do the manual cleaning work with the instruments, to carry out other jobs. Moreover, the short treating time will imply that the dentist should not have at disposal as many sets of instruments as if they were cleaned conventionally. It should be mentioned, however, that according to the invention it is preferred to make use of an autoclavation time longer than the briefest possible, viz. at a moderate autoclavation temperature, e.g. 121° C. with an associated overpressure of one bar through approximately 20 minutes. It is not unknown that customers can be attracted by autoclaves operable to treat the instruments at reduced time with the use of a higher temperature, but it seems certain that the durability of the instruments will then be noticeably reduced, primarily by a breaking down their gaskets. It will be more economical to procure the extra instruments required due to a longer autoclavation time, but in return they can be expected to have a much longer operational lifetime.

In the following the invention is described in more detail with reference to the drawing, in which:

FIG. 1 is a sectional side view of an apparatus according to an embodiment of the invention;

FIG. 2 is a sectional side view of a holding stub with a contra angle mounted thereon;

FIGS. 4 and 5 are illustrations of a preferred design of an operative unit in the apparatus;

FIG. 6 is a perspective view of a preferred design of the apparatus; and

FIG. 7 is a diagram illustrating the process in the apparatus.

Figure 3:
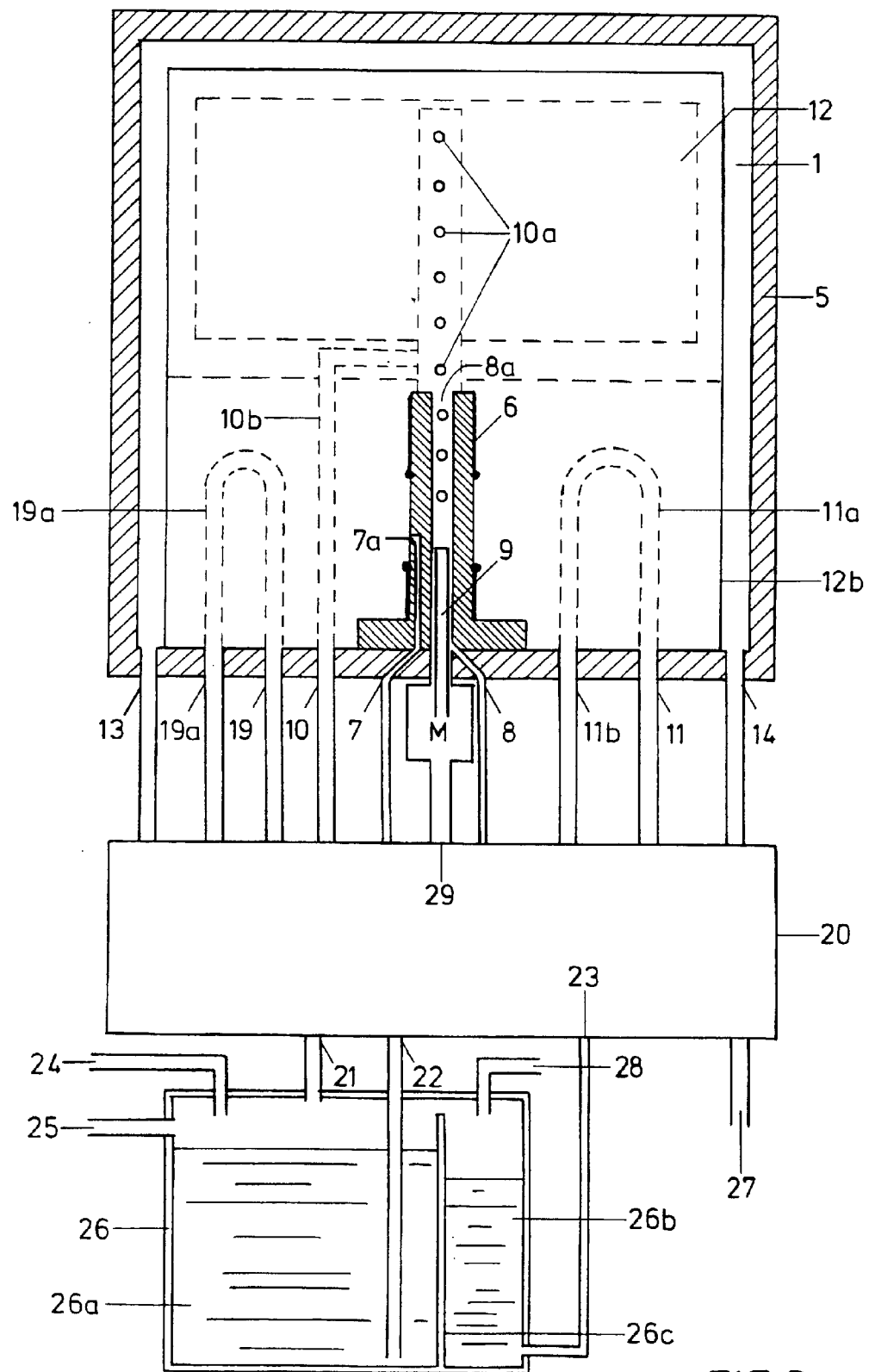
FIG. 3 is a diagram of an apparatus according to the invention.

FIG. 1 shows an apparatus housing portion with an autoclave chamber 1 having a lid 2 suspended in a hinge 3 and held by a lid lock 4. The chamber 1 is insulated by an insulation material 5. A gasket 2a seated in the insulation makes the lid close tightly. On the rear wall of the chamber 1 a holding stub 6 is fitted, surrounded by two gaskets 6a, 6b. For simplicity, only one stub is shown, but there may well be more of them. The holding stub has a bore 8a, holding a driving shaft 9. This shaft projects through a bearing 9a provided at the outside of the wall. The holding stub 6 also has a blow-in channel 7a connected through the wall with an inlet stub 7 for steam or air. The bore 8a is connected with another blow- in channel 8b in connection with an inlet stub 8 for oil or air.

The autoclave chamber 1 houses a heating body 12 in mechanical connection with a heating block 12a, in which there is a longitudinal bore 10b connected with an inlet stub 10 for air and water. The top portion of the heating block 10a is provided with a number of vertical bores 10a connected to the bore 10b. A smaller heating block 12b is secured to the underside of the block 12a and provided with a longitudinal bore 11a which, at the outside of the chamber 1, is connected to an inlet stub 11 for oil or air. The more detailed design of the heating blocks 12a and 12b will be described in connection with FIG. 3.

At the bottom of the autoclave chamber 1 a liquid drain 14 is provided, with a pressure outlet stub 13 mounted thereabove. Mounted at the upper left hand corner of the autoclave chamber is a safety valve comprising a pressure outlet stub 15 and a ball 15a which, by the action of a spring 15b is urged against an O-ring 15c with a pressure set by a screw 15d.

FIG. 2 illustrates a holding stub 6 with a contra angle 16 mounted thereon. As it will be noted, the blow-in channel 7a communicates with a spray channel 17 debouching at 17a. Moreover, the driving shaft 9 is mechanically connected with a drive shaft 18 in the contra angle, this shaft projecting to a drill bit holder 18a.

The plan view of FIG. 3 shows details not appearing from FIG. 1. The channel 11a in the block 12b as connected with the oil/air intake 11 is returned to an oil/air outlet stub 11b. Another channel 19b from a water/-air inlet stub 19, for heating purposes, is looped back to an outlet stub 19a. All of said stubs are, via tight conduits such as hoses or pipes, connected with a control unit 20 housing control electronics and a valve equipment.

Shown underneath the control unit 20 is a water and oil tank 26. For simplicity, the tank 26 is seen from the side while the autoclave chamber is seen from above. The tank is divided in two sections by means of a separation plate 26c so the liquids will not be mixed. To the left is a water reservoir 26a and to the right an oil reservoir 26b. The narrow passage at the top edge of the plate 26c ensures an equal pressure in both sections. Several pipe connections are provided at the top of the tank. Water is supplied to the water section 26a via a water pipe 24, while a pipe 25 is for supply of compressed air. Oil is supplied through an oil supply pipe 28. There are three outlets from the tank, all connected to the control unit 20. An air pipe 21 provides for compressed air, a water pipe 22 for water, and an oil pipe 23 for oil to the control unit 20. At the control unit bottom, to the right, a drain pipe 27 is provided. A central pipe 29 projects from the upper part of the control unit, and thereabove a locality M indicates where a driving connection to the driving shaft 9 can be arranged. Actual driving may be achieved by an electric motor.

The apparatus will function as now described, provided an air pressure of some 2 bar being supplied to the air pipe 25, and provided the autoclave being connected to a voltage supply. It is also provided that both the oil inlet pipe 28 and the water inlet pipe 24 are closed, so that the compressed air cannot escape therethrough.

A contra-angle 16 to be cleaned and sterilized is mounted on the holding stub 6 in the autoclave chamber 1, ad the lid 2 is closed and locked by the lid lock 4. The autoclave chamber is now pressure tight, and the process can begin. The autoclave comprises two separate pipe circuits for cleaning and sterilizing spray channels 17 and the mechanics 18 in the contra angle 16, respectively. Thus, the spray channels 17 can be supplied with steam or hot air only, while the mechanics can exposed to oil or hot air only. The process may proceed in different manners, as it is possible, via the control unit 20, to actuate the oil and air supply to the inlet 8b, the steam or air supply to the bores 10a and the mechanical motion of the driving shaft 9, all for a desired period of time and in a pulsating or continuous manner.

The sterilization of the contra-angle is effected by heating the autoclave chamber by means of the heating body 12. Via a control circuit the temperature in the autoclave chamber is kept at approximately 122° C. Another temperature can be chosen, if desired. From the water tank 26a, by means of the pressure therein, water is pressed up through the water supply pipe 22. Via the control unit 20 the water is conducted to the heating inlet stub 19 for air and water and further through the channel 19b, in which the water is rapidly heated and converted to steam. Via the outlet stub 19a the steam is fed to the control unit 20 which conducts it further to the steam/air inlet stub 7 and the blow-in channel 7a, from which the steam proceeds through the spray channels 17 in the contra angle 16. The steam flow causes any possible dirt in the spray channel to be loosened and blown out together with the steam. Likewise, water is supplied from the control unit 20 to the air/water inlet stub 10, from which the water continues through the longitudinal bore 10b, in which it is heated and converted into steam. This steam is blown out through the holes 10a, whereby an external heating of the contra angle 16 is achieved.

The pressure in the autoclave chamber is measured by a sensor (not shown), and it is kept constant during the process by bleeding any overpressure through the pressure outlet stub 13, the control unit 20 and the outlet pipe 27. The overpressure in the chamber will be about 1.1 bar above ambient pressure for a temperature of about 122° C., at which the contra angle is sterilized.

Cleaning and lubrication of the mechanics 18 of the contra-angle is brought about by pressing oil from the tank 26b through the oil supply pipe 23 up to the control unit 20 and therefrom further to the oil/air inlet stub 11, through the channel 11a in the heating block 12b, in which the oil is heated. The warm oil flows further to the control unit 20 via the oil/air outlet stub 11b. From the unit 20 the oil is let further through the oil/air inlet stub 8 and into the mechanics 18 of the contra angle 16. The heated oil causes the old oil in the mechanics to be pressed out, viz. through an outermost small channel in the contra angle (not shown). It has been found that in the initial phase of the cleaning process of the mechanics 18 it is suitable to supply warm oil, which will loosen dried or adhering oil from the mechanical parts, while a corresponding supply of oil for lubrication purposes can be effected towards the end of the process.

During the cleaning process the rotary mechanics 18 in the contra-angle 16 is set in motion by means of an electromotor driving the shaft 9 in the point M. If a turbine is cleaned, the driving shaft 9 is left out and the turbine is set in motion by means of compressed air which, controlled by the control unit 20 and via the central tube 29, is blown into the bore 8a. A lubrication of the turbine in the contra angle may be effected through the oil/air inlet stub 8 and the blow-in pipe 8b.

When the process has been going on for a certain period of time, a drying of the contra-angle is initiated automatically. To this effect the water supply is stopped. Then air from the compressed air pipe 21 is blown through the control unit 20, the air/water heating inlet stub 19, the channel 19*b*, the air/water outlet stub 19*a* and the control unit 20, from which the heated air is distributed to the air/water inlet stub 10, the steam/-air blow-in stub 7 and further to the blow-out pipe 7*a*, from which the air passes to the spray channel 17 to dry the same.

The warm air as distributed to the holes 10*a* via the air/water inlet stub 10 and the longitudinal bore 10*b* will soon dry the exterior of the contra-angle. If a turbine is mounted on the holding stub 6, it is also possible to blow warm air into the center pipe 29, from which the air may continue into and fry the turbine.

Immediately after the final drying of the instrument or instruments, the water and the overpressure are removed from the chamber 1 through the bottom drain 14 which, via the control unit 20, is connected to the outlet pipe 27. The lid 2 can now be opened, when the lock 4 has been released. Thereafter the still warm instrument or instruments can be taken out, and one or more new instruments can be mounted in the autoclave chamber, whereafter the process can be repeated.

Tests have shown that en efficient cleaning, lubrication and sterilization of one or more contra angles can be effected in e.g. 18–20 minutes.

As apparent from the drawing, the autoclave chamber can be made very compact, and according to the invention the chamber is even insulated, implying that an auto-claving can be effected with a minimum of energy consumption, as the required temperature and pressure is rapidly established. Tests have shown that the apparatus may function with an energy consumption of about 300 W, which is less than one fourth of the consumption of traditional autoclaves. Moreover, as the process time is reduced from about 50 to about 18 minutes there will be no need for particularly many sets of hand instruments. The secretary normally attending to the relevant work may, with this apparatus, reduce the process time noticeably, as there is only one and not the usual three operations to attend to, and this operation will run automatically, without being supervised.

FIGS. 4–6 show a preferred embodiment of the treating and autoclaving unit, here made as a cylinder 30 mounted in a heat insulated housing 32. At its rear end the cylinder is tightly closed by an end plate 34 having throughlet stubs 36 for the different media and a central hole for the throughlet of a rod 38, the front end of which is connected with a circular plate 40 carrying the holding stubs for the implements to be treated. These stubs are connected with the throughlet stubs by means of hoses 42. Moreover, behind each of the stubs 6 there is mounted an air turbine 44 which is air supplied through a flexible hose for driving the drive shaft 9 of the stub.

By means of the rod 38, the mounting plate 40 is displaceable between the foremost position shown in FIG. 4 and the retracted position shown in FIG. 5. The shifting between the positions is effected by means of a pair of exterior cylinders 46, the through-going piston rods 48 of which having at the rear a cross piece 50, to which the rod 38 is secured. At the front, the piston rods 48 have bearing heads 52 carrying between them a pivotable front cover 54 for tightly closing the front end of the cylinder. Such a closing will occur automatically, when the entire system 40, 38, 50, 48, 54 is displaced rearwardly to the position shown in FIG. 5. In the open position, FIG. 4, there is ample space for mounting and removal of the instruments.

In this embodiment the special heating blocks 12*a* and 12*b*, FIG. 1, have been renounced, as it has been found sufficient to make use of a lower, exterior heating body 56. The cylinder 30 is made of a heat conducting material such as aluminium and is, as mentioned, placed in heat insulated surroundings. The water supply to the chamber takes place through the instruments to be cleaned.

The housing 32, FIG. 6, also contains the entire required supply and control equipment as well as relevant operation buttons and indicators. The operative functions are widely the same as described above, yet with the exception that hot steam is not used; instead, warm water is used, produced by supplying the water through a heat exchange pipe 58 cooperating with the heating body 56. It has been found that water at 60–70° C. is preferable to hot steam, which may cause a coagulation of the materials to be cleaned out.

Because of the small size of the integrated autoclave, the unit may be made as a compact apparatus for loose mounting on a table, with a hose connection to a compressed air source. The indicator equipment may comprise gauges for the liquid level in the water and oil tank, respectively.

FIG. 7 shows a process diagram for a preferred course of the automatically controlled process. At the background of the explanation already given, the diagram will be self-explanatory. Typically, the process time may be approximately 20 minutes, and the consumption of water and oil may be 40 ml and 1 ml, respectively, the latter for the treatment of three instruments at the same time.

What is claimed is:

1. An apparatus for cleaning dental handpieces, comprising: at least one holding stub for receiving a handpiece having interior channel means which open externally of the handpiece, said at least one holding stub having means for connecting the interior channel means of the handpiece with separate sources of cleaning and lubrication media, and being mounted in a closable treating autoclave pressure chamber means for externally treating the dental handpieces with steam;

a supply of liquid at a temperature below 100° C., said supply being connected said means for connecting of the at least one holding stub for supplying liquid to the interior channel means of the handpiece at a temperature below 100° C. for preventing coagulation of materials to be cleaned out of the handpiece;

heating means arranged for heating a bottom region of said chamber means and for converting the liquid supplied to the bottom region from the interior channel means of the handpiece into steam at an elevated temperature and an elevated pressure in a space surrounding the dental handpiece on the at least one holding stub, thereby effectively enabling the closable treating autoclave pressure chamber means to act as an autoclave for surrounding and externally heating the handpiece with steam;

wherein said bottom region of the chamber means has a liquid drain outlet for draining liquid therefrom; and wherein an upper region of said chamber means has a pressure relief valve.

2. An apparatus according to claim 1, in which there is mounted, in connection with the heating means, a heat exchanger for heating of water from an associated water supply, this exchanger being connected with the holding stubs for feeding water to the autoclave pressure chamber means through the internal channels of the handpieces.

3. An apparatus according to claim 2, comprising control means for effecting a pulsating supply of the water.

4. An apparatus according to claim 1, comprising control means for effecting a brief dosing of lubrication oil to the handpieces both at the beginning of a cleaning cycle and at the end of an associated autoclaving cycle.

5. An apparatus according to claim 1, in which the autoclave pressure treating chamber means is made as a cylinder with an openable front cover and a closed rear end, while a wall portion of said autoclave pressure chamber means carrying the holding stubs is displaceable in the cylinder between a foremost change-out position and a rear treatment position.

6. An apparatus according to claim 5, in which the connections to the holding stubs comprise flexible hoses extending between the rear side of the stub mounting wall portion and throughlet stubs in the rigid rear wall of the cylinder.

7. An apparatus according to claim 5, in which driving means for rotation of the rotating parts of the handpieces comprise air turbine means located at the rear side of the mounting wall portion.

8. An apparatus according to claim 5, in which the front cover is in such a rigid connection with the mounting wall portion that it is parallelly displaced between a fully closed and a widely open position in response to displacement of the wall portion.

9. An apparatus according to claim 8, in which the front cover is mounted in a diagonally tiltable manner between the front ends of opposed external piston rods belonging to respective opening and closing cylinders.

10. An apparatus according to claim 1, with a cabinet comprising both the treating autoclave pressure chamber means and supply tanks for water and oil as well as the required control equipment for effecting a complete cleaning, lubrication and sterilization cycle.

11. A method of cleaning dental handpieces, comprising the steps of:

mounting a handpiece on a socket member having an external connection to a water supply source;

bringing the socket member and handpiece into a closed, treating chamber having heating means arranged at a bottom side of the chamber;

injecting water of a temperature lower than 100° C. from said water supply source through the internal channel system of the handpiece into said treating chamber; and subsequent to said injecting, actuating said heating means to effect boiling of the water injected into the treating chamber from the handpiece and maintaining this actuation to achieve steam autoclaving of the handpiece at elevated temperature and pressure inside said chamber for a preselected period of time, so that the interior of the handpiece is cleaned by liquid and the exterior by steam;

further comprising the preliminary step of supplying lubricating oil from a lubricating oil source to internal mechanics of said handpiece near an end of said preselected time period.

12. The method according to claim 11, further comprising the step of supplying lubricating oil from a lubricating oil source to internal mechanics of said handpiece near an end of said preselected period of time.

13. The method according to claim 11, further comprising the step of supplying lubricating oil from a lubricating oil source to internal mechanics of said handpiece near an end of said preselected period of time.

14. The method according to claim 11, wherein the temperature of the water injected is in the range of 60–70° C.

* * * * *